(12) United States Patent
Lenich et al.

(10) Patent No.: US 12,109,077 B2
(45) Date of Patent: Oct. 8, 2024

(54) DEVICE FOR MOVING A MEDICAL OBJECT AND METHOD FOR PROVIDING A SIGNAL

(71) Applicant: Siemens Healthcare GmbH, Erlangen (DE)

(72) Inventors: Tobias Lenich, Nuremberg (DE); Trixi Leistner, Erlangen (DE); Stanislav Tashenov, Heroldsbach (DE)

(73) Assignee: Siemens Healthineers AG, Forchheim (DE)

( * ) Notice: Subject to any disclaimer, the term of this patent is extended or adjusted under 35 U.S.C. 154(b) by 405 days.

(21) Appl. No.: 17/480,381

(22) Filed: Sep. 21, 2021

(65) Prior Publication Data

US 2022/0087776 A1 Mar. 24, 2022

(30) Foreign Application Priority Data

Sep. 24, 2020 (DE) ..................... 10 2020 211 999.6

(51) Int. Cl.
*A61B 90/50* (2016.01)
*A61B 34/30* (2016.01)
*A61B 90/00* (2016.01)

(52) U.S. Cl.
CPC .............. *A61B 90/50* (2016.02); *A61B 34/30* (2016.02); *A61B 2090/3983* (2016.02); *A61B 2090/5025* (2016.02)

(58) Field of Classification Search
CPC . A61B 90/50; A61B 34/30; A61B 2090/3983; A61B 2090/5025;
(Continued)

(56) References Cited

U.S. PATENT DOCUMENTS 6,726,675 B1 4/2004 Beyar
10,342,595 B2 7/2019 Hancock et al.
(Continued)

FOREIGN PATENT DOCUMENTS

AU 2017388217 A1 5/2019
CN 102046081 A 5/2011
(Continued)

OTHER PUBLICATIONS

Özin et al., Friction force evaluation for grasping in minimally invasive surgery, Oct. 31, 2018, Dept. of Mech. Eng., Istanbul Technical University, Gumussuyu,34437, Beyoglu, Istanbul, Turkey, p. 167-173. (Year: 2018).*
(Continued)

*Primary Examiner* — Kidest Bahta
(74) *Attorney, Agent, or Firm* — Lempia Summerfield Katz LLC

(57) ABSTRACT

A device for moving a medical object, the device including a mover device and a sensor unit. The mover device is configured to hold and/or move a medical object at least partially disposed in the mover device by transmitting a force. The sensor unit is configured to detect a counterforce exerted by the medical object on the mover device and acting in the opposite direction to the force. The medical object is at least partially disposed in an examination subject. The device is configured to provide a signal as a function of the counterforce. The mover device is configured to move the medical object as a function of the signal.

18 Claims, 6 Drawing Sheets

(58) Field of Classification Search
CPC .............. A61B 90/37; A61B 2090/376; A61B 2090/378; A61B 2034/301; A61B 2090/065; A61B 2090/3762; A61B 34/20; A61B 2034/2065; A61M 25/0113; A61M 25/0105; A61M 2025/0166; A61M 2205/332

See application file for complete search history.

(56) References Cited

U.S. PATENT DOCUMENTS

| | | |
|---|---|---|
| 2005/0197557 A1 | 9/2005 | Strommer |
| 2009/0131955 A1 | 5/2009 | Wenderow |
| 2009/0247993 A1 | 10/2009 | Kirschenman |
| 2012/0071821 A1 | 3/2012 | Yu |
| 2013/0190726 A1 | 7/2013 | Kesner et al. |
| 2014/0058406 A1 | 2/2014 | Tsekos |
| 2015/0134017 A1* | 5/2015 | Chellaoui .......... A61B 17/8872 606/86 R |
| 2015/0142013 A1 | 5/2015 | Tanner |
| 2017/0151025 A1 | 6/2017 | Mewes |
| 2019/0355278 A1 | 11/2019 | Sainsbury |
| 2020/0121556 A1 | 4/2020 | Tian |
| 2020/0297239 A1* | 9/2020 | Olson ................. A61B 5/4839 |
| 2020/0345305 A1* | 11/2020 | Gelman ............. A61B 18/1492 |

FOREIGN PATENT DOCUMENTS

| | | |
|---|---|---|
| CN | 104736097 A | 6/2015 |
| CN | 106914893 A | 7/2017 |
| CN | 108882966 A | 11/2018 |
| DE | 10303270 A1 | 8/2004 |
| EP | 3562423 A1 | 11/2019 |
| JP | 2016221025 A | 12/2016 |
| WO | 2018125917 A1 | 7/2018 |

OTHER PUBLICATIONS

Takashima et al. Contact and friction between catheter and blood vessel, Mar. 29, 2006, Institute for Frontier Medical Sciences, Kyoto University 53 Kawahara-cho, p. 319-328. (Year: 2006).*

Cheng et al., Feedforward Coordinate Control of a Robotic Cell Injection Catheter, Sep. 13, 2017, Saga Journals, p. 1319-1330 (Year: 2017).*

Cercenelli et al., Cath ROB: A Highly Compact and Versatile Remote Catheter Navigation System, May 25, 2017, Applied Bionics and Biomechanics vol. 2017, Article ID 2712453, pp. 1-13. (Year: 2017).*

Alma Josephine Marie Melcop, "Comparative examination of the rigidity of guide wires in minimally invasive catheter systems—Experimental in vitro study of 21 guide wires—" Dissertation LMU Munchen, Section 1.5.4, 2018. pp. 1-88 with abstract.

German Office Action for German Application No. 10 2020 211 999.6 dated Jul. 23, 2021.

* cited by examiner

DEVICE FOR MOVING A MEDICAL OBJECT AND METHOD FOR PROVIDING A SIGNAL

CROSS REFERENCE TO RELATED APPLICATIONS

This application claims the benefit of DE 102020211999.6 filed on Sep. 24, 2020, which is hereby incorporated by reference in its entirety.

FIELD

Embodiments relate to a device and method for moving a medical object.

BACKGROUND

Interventional medical procedures in and/or across a hollow organ of an examination subject frequently require a medical object to be introduced, for example percutaneously, into the hollow organ. In such procedures, the medical object may be configured for example as an, for example elongate, surgical and/or diagnostic instrument. The hollow organ may be for example a vessel section, for example a vein and/or an artery, and/or the heart and/or a lung of the examination subject.

Furthermore, it is often necessary for a successful diagnosis and/or treatment to move at least a part of the medical object forward toward a target region that is to be treated in the hollow organ, for example the vessel section. When the medical object is being moved and/or positioned, it may happen that the medical object, for example a distal end portion of the medical object, encounters an obstacle in the hollow organ. This may often cause a resistance, for example a counterforce, to act on the medical object, the resistance acting in the opposite direction to a force that is applied to the medical object, by a user for example. However, it is often difficult in such a situation for the user to detect the counterforce and respond to it accordingly. If this counterforce goes unnoticed and/or is not taken into account during a further movement of the medical object, it may disadvantageously result in a puncturing of a structure of the examination subject, for example in a perforation, and subsequently lead to an injury.

Furthermore, a frictional force between the medical object and the hollow organ may also cause the counterforce. Depending on the field of application, the medical objects often have a hydrophilic and/or hydrophobic surface, that may be negatively affected as a result of external mechanical and/or chemical and/or electromagnetic action.

It is known from the publication by A. J. M. Melcop, "*Vergleichende Untersuchung der Steifigkeit von Führungsdrähten minimalinvasiver Kathetersysteme—Experimentelle in-vitro-Studie an* 21 *Führungsdrähten—*" ("*Comparative investigation of the stiffness of guidewires of minimally invasive catheter systems—Experimental in-vitro study based on* 21 *guidewires*"), doctoral thesis, LMU Munich, 2018, that a coefficient of friction of the medical object may be reduced by a factor of 2 by a hydrophobic coating and by a factor of 3 by a hydrophilic coating. The publication discloses that hydrophilic coatings for example may be easily damaged.

This may disadvantageously lead to an increase in the frictional force between the medical object and the hollow organ, as a result of which the force required to move the medical object must be increased. Consequently, this often also increases the risk of injury for the examination subject.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a safe and at the same time precise movement of a medical object.

Embodiments relate to a device for moving a medical object. The device includes a mover device and a sensor unit. The mover device is configured to hold and/or move a medical object at least partially disposed in the mover device by transmission of a force. The sensor unit is configured to detect a counterforce exerted by the medical object on the mover device and acting in the opposite direction to the force. The medical object is at least partially disposed in the examination subject. The device is configured to provide a signal as a function of the counterforce. The mover device is also configured to move the medical object as a function of the signal.

The medical object may be configured for example as an, for example elongate, surgical and/or diagnostic instrument. For example, the medical object may be flexible and/or rigid, at least in sections. The medical object may be configured for example as a catheter and/or an endoscope and/or a guidewire.

The device may additionally include a processing unit that is configured to control the device and/or its components, for example the mover device.

The mover device may be a robotic device that is configured to allow remote manipulation of the medical object, for example a catheter robot. The mover device is disposed outside of the examination subject. The mover device may include an, for example movable and/or displaceable, securing element. The mover device may also include a cassette element that is configured to accommodate at least a part of the medical object. The mover device may include a mover element that is fixedly mounted on the securing element, for example a stand and/or a robotic arm. The securing element may be configured to secure the mover element to a patient support and positioning device. In addition, the mover element may include at least one actuator element, for example an electric motor. The processing unit is configured to control the actuator element. The cassette element may be couplable, for example mechanically and/or electromagnetically and/or pneumatically, to the mover element, for example to the at least one actuator element. The cassette element may additionally include at least one transmission element that is movable as a result of the coupling between the cassette element and the mover element, for example the at least one actuator element. For example, the at least one transmission element may be movably coupled to the at least one actuator element. The transmission element is configured to transmit a movement, for example the force, of the actuator element to the medical object in such a way that the medical object is moved along a longitudinal extension direction of the medical object and/or that the medical object is rotated around its longitudinal extension direction. The at least one transmission element may include for example a roller and/or drum and/or shield and/or shearing plate. The transmission element may be configured to hold the medical object, for example in a stable manner, by transmitting the force. The holding of the medical object may for example include a stationary positioning of the medical object in relation to the mover device.

The mover element may include a plurality of, for example independently controllable, actuator elements. The cassette element may include a plurality of transmission elements, for example at least one movably coupled transmission element for each of the actuator elements. This may facilitate an, for example independent and/or simultaneous, movement of the medical object along different degrees of freedom.

The medical object may be introduced by an introducer sheath at least partially into the examination subject in such a way that a distal end portion of the medical object, for example a tip, is disposed inside the examination subject. The examination subject may be for example a human and/or animal patient and/or a vessel phantom. The examination subject may have a hollow organ, for example a vessel section, for example a vein and/or an artery, and/or a heart and/or a lung, in which the distal end portion of the medical object may be disposed.

The sensor unit may include a force transducer that is configured to detect the counterforce exerted by the medical object on the force transducer. The sensor unit may for example include an electromagnetic, for example capacitive and/or resistive and/or piezoelectric and/or electrodynamic, and/or mechanical and/or optical force transducer. The force transducer may also be at least partially integrated into the actuator element and/or the transmission element, for example as a torque sensor. The counterforce may act in the opposite direction to the force for holding and/or moving, for example for translating and/or rotating, the medical object. The sensor unit, for example the force transducer, may be configured to provide a sensor signal as a function of the detected counterforce. The sensor signal may include information relating to a direction and/or a magnitude of the counterforce. The sensor signal may also be time-resolved. The sensor signal may additionally include an operating parameter of the mover device and/or an operating parameter of the medical object and/or a physiological parameter of the examination subject, for example as metadata.

The device, for example the processing unit, may be configured to provide the signal as a function of the counterforce, for example as a function of the sensor signal. For example, the device may be configured to provide the sensor signal as the signal. The signal may include information relating to a direction and/or a magnitude of the counterforce.

The mover device may be configured to move the medical object as a function of the signal in such a way that the counterforce is reduced. For this purpose, the processing unit may be configured to compare the signal with a predefined threshold value. The mover device may be configured to respond to an exceeding of the threshold value by the signal by adjusting the, for example current, movement of the medical object as a function of the signal. For example, the mover device may be configured to respond to a detection of a counterforce by the sensor unit by slowing down, for example by stopping, an, for example current, movement of the medical object. Alternatively, or in addition, the mover device may be configured, upon detecting a counterforce by the sensor unit, to adjust the, for example current, movement of the medical object as a function of the signal. For example, the mover device may be configured to adjust, for example reverse, a movement direction of the movement of the medical object as a function of the signal. The mover device may also be configured to adjust, for example reduce, a motion speed of the movement of the medical object as a function of the signal.

The medical object may be configured as deformable, at least in sections, for example by a Bowden cable. The distal end portion of the medical object for example may be deformable. The mover device may be configured to control an at least section-wise deformation of the medical object, for example of the distal end portion, as a function of the signal. Advantageously, this may allow the movement direction of the medical object to be adjustable at the distal end portion.

Embodiments provide the medical object to be moved in a particularly reliable, for example robotic, manner by the mover device, it being possible to adjust and/or stop the movement of the medical object if a counterforce is detected. Advantageously, this enables the detected counterforce to be reduced, as a result of which a risk of injury to the examination subject may be reduced. Furthermore, a reliable detection of the counterforce is possible by the device, for example compared to a manual moving and/or holding of the medical object.

In an embodiment of the device, the device may additionally include a processing unit and a reference unit. The medical object, for example a distal end portion, may be disposed in a hollow organ of the examination subject. The reference unit may be configured to detect at least one coefficient of friction of the medical object on the mover device and/or on an introducer sheath for introducing the medical object into the examination subject. In addition, the processing unit may be configured to simulate a virtual frictional force between the medical object and the hollow organ on the basis of the at least one coefficient of friction. The processing unit may be configured to identify or rule out a frictional force between the hollow organ and the medical object as the origin of the counterforce based on a comparison between the counterforce and the virtual frictional force. In addition, the processing unit may be configured to provide the signal as a function of the origin of the counterforce.

The reference unit may for example include a friction sensor and/or a surface sensor. The friction sensor may include for example a friction wheel and/or a friction roller and/or a friction plate that comes into mechanical contact with the surface of the medical object on the introducer sheath and/or on the mover device. The friction sensor may be configured to determine the at least one coefficient of friction via a friction resistance of the friction wheel and/or the friction roller and/or the friction plate compared to the surface of the medical object.

In an embodiment, the friction sensor may be configured to transmit a reference force acting in the opposite direction to the force to the medical object by the friction wheel and/or the friction roller and/or the friction plate. The sensor unit may be configured to detect a deviation compared to the reference force. The reference unit may be configured to determine the at least one coefficient of friction of the surface of the medical object based on the detected deviation.

In an embodiment, the friction sensor may be configured to detect a slippage at the surface of the medical object. For this purpose, the friction sensor may be configured to transmit the reference force along or counter to the force onto the medical object by the friction wheel and/or the friction roller and/or the friction plate. The friction sensor may also be configured to detect a slippage of the friction wheel and/or the friction roller and/or the friction plate, for example quantitatively. The reference unit may be configured to determine the at least one coefficient of friction of the surface of the medical object based on the detected slippage. For example, the friction sensor may be at least partially integrated into the transmission element. The transmission element may act in addition as a friction wheel and/or friction roller and/or friction plate.

The surface sensor may for example include an electromagnetic and/or optical and/or mechanical and/or ultrasound-based sensor that is configured to detect a surface texture of the medical object on the introducer sheath and/or on the mover device. The surface sensor may be configured to detect a material property of the surface of the medical object, for example quantitatively. In order to reduce a frictional force between the medical object and the examination subject, for example the hollow organ, the medical object may include an, for example hydrophobic or hydrophilic, coating and/or surface structure. The surface sensor may be configured to detect a change in the surface of the medical object, for example in the coating and/or surface structure, compared to a reference value. The reference value may characterize a condition of the surface of the medical object prior to its being introduced into the examination subject. For example, the surface sensor may be configured to detect a reduction in a layer thickness of the coating of the medical object. The reference unit may be configured to determine the at least one coefficient of friction of the medical object based on the surface texture and/or change in the surface of the medical object detected by the surface sensor.

The processing unit may be configured to simulate the virtual frictional force between the hollow organ and the medical object at least partially disposed therein on the basis of the at least one coefficient of friction. The processing unit may be configured to simulate the virtual frictional force in addition based on a parameter of the medical object, for example an operating parameter and/or a material parameter, and/or an operating parameter of the mover device and/or a physiological parameter of the examination subject.

The processing unit may be configured to compare the counterforce with the virtual frictional force. The processing unit may be configured to identify the frictional force between the hollow organ and the medical object as the, for example sole, origin of the counterforce if the counterforce substantially corresponds to the virtual frictional force. For example, the processing unit may be configured to determine a deviation between the counterforce and the virtual frictional force. The processing unit may also be configured to identify the frictional force between the hollow organ and the medical object as the, for example sole, origin of the counterforce if the deviation lies below a predefined threshold value.

The processing unit may be configured to rule out the frictional force as the, for example sole, origin of the counterforce if a deviation between the counterforce and the virtual frictional force exceeds the predefined threshold value. The threshold value may be predefined as a function of the parameter of the medical object and/or of the operating parameter of the mover device and/or of the physiological parameter of the examination subject. Alternatively, or in addition, the threshold value in relation to the deviation between the counterforce and the virtual frictional force may be predefinable by way of an input by a user by an input unit.

In addition, the processing unit may be configured to provide the signal including information on the origin of the counterforce. The providing of the signal may for example include storing the same on a computer-readable storage medium and/or displaying the same on a visualization unit and/or transferring the same to the mover device.

Embodiment provide for the frictional force to be identified or ruled out as the, for example sole, origin of the counterforce. This may allow the movement of the medical object to be adjusted in a particularly precise manner by the mover device as a function of the origin of the counterforce.

In an embodiment of the device, the device may be configured to receive a dataset, the dataset containing an image of the examination subject. The device may be configured to determine a spatial positioning of a distal end portion of the medical object with respect to the dataset. In addition, the device may be configured to identify an origin of the counterforce as a function of the counterforce, the spatial positioning of the distal end portion and the dataset. The device may be configured to provide the signal as a function of the origin of the counterforce.

The receiving of the dataset may for example include an acquisition thereof and/or a readout thereof from a computer-readable data memory and/or a receiving thereof from a data storage unit, for example a database. The dataset may be provided by a provider unit of a medical imaging device for acquiring and/or providing the dataset. The medical imaging device may for example include a magnetic resonance tomography (MRT) system and/or a computed tomography (CT) system and/or a medical x-ray device, for example a medical C-arm x-ray device, and/or an ultrasound device and/or a positron-emission tomography (PET) system.

The dataset may contain a two-dimensional and/or three-dimensional image of the examination subject, for example of the hollow organ. The dataset may image the examination subject in time-resolved form and/or preoperatively, for example prior to the introduction of the medical object. In addition, the dataset may be registered with a coordinate system of the examination subject. The dataset may contain a post-contrast image of the examination subject, for example of the hollow organ, a contrast agent flow in the examination subject, for example the hollow organ, being imaged in the dataset, for example in time-resolved form. This may provide a precise identification of time-invariable structures in the examination subject, for example on the basis of time intensity curves of image elements (pixels/voxels) of the dataset.

In addition, the dataset may contain an, for example two-dimensional and/or three-dimensional, model of the examination subject, for example of the hollow organ, for example a centerline model and/or a volume mesh model.

The processing unit may be configured to determine the spatial positioning, for example a spatial position and/or orientation, of the distal end portion of the medical object with respect to the dataset. The processing unit may for example be configured to determine a length of the medical object between the distal end portion of the medical object and the introducer sheath and/or the mover device based on an operating parameter of the mover device. The operating parameter of the mover device may contain information relating to the previous movement of the medical object, for example to a translation and/or rotation, by the mover device. The processing unit may be configured to determine a spatial trajectory of the medical object in the examination subject, for example the hollow organ, based on the dataset and the length of the medical object between the distal end portion of the medical object and the introducer sheath and/or the mover device.

Alternatively, or in addition, the device may include a localization unit. The localization unit may for example include an electromagnetic and/or ultrasound-based sensor that is configured to detect the spatial positioning of the distal end portion, for example in the coordinate system of the examination subject. The localization unit may be disposed for example on the patient support and positioning device and/or on the mover device and/or on the introducer sheath and/or on the medical object.

In addition, the processing unit may be configured to determine a change in the spatial positioning of the distal end portion with respect to the dataset. The processing unit may be configured to compare the spatial positioning of the distal end portion, for example the change in the spatial positioning of the distal end portion, with a control default of the mover device for moving and/or holding the medical object, for example for positioning the distal end portion in the examination subject.

The processing unit may be configured to identify the origin of the counterforce as a function of the counterforce, for example of a direction and/or a magnitude of the counterforce, of the spatial positioning of the distal end portion with respect to the dataset, and of the dataset. Identifying the origin of the counterforce may in this case include identifying or ruling out the frictional force between the medical object and the examination subject, for example the hollow organ, as the, for example sole, origin of the counterforce.

If a change in the spatial positioning of the distal end portion of the medical object is determined in the presence of a counterforce, that change deviates from the control default of the mover device, the processing unit may be configured to identify the frictional force between the medical object and the hollow organ as the, for example sole, origin of the counterforce. If no change in the spatial positioning of the distal end portion of the medical object is determined in the presence of a counterforce, where the control default of the mover device specifies a force for moving the medical object, the processing unit may be configured to identify the origin of the counterforce additionally on the basis of the dataset. The processing unit may be configured to identify an incorrect positioning, for example an incorrect orientation, of the distal end portion of the medical object in the hollow organ based on the, for example current, spatial positioning with respect to the dataset as the origin of the counterforce.

The processing unit may be configured to simulate the virtual frictional force in addition based on the spatial positioning of the distal end portion. An accuracy of the simulation may be improved as a result.

Embodiments provide an origin of the counterforce to be identified taking into account the, for example current, spatial positioning of the distal end portion of the medical object, the dataset and the detected counterforce.

The processing unit may be configured to provide the signal containing information on the origin of the counterforce. Providing the signal may for example include storing the same on a computer-readable storage medium and/or displaying the same on a visualization unit and/or transferring the same to the mover device.

In an embodiment, the reference unit may be configured to detect a plurality of coefficients of friction along a longitudinal extension direction of the medical object. The medical object may be movable relative to the reference unit by the mover device. The processing unit may be configured to simulate the virtual frictional force as a function of the spatial positioning of the distal end portion of the medical object in the examination subject, for example on the basis of the dataset, and of the plurality of coefficients of friction.

The reference unit may be configured to detect the plurality of coefficients of friction along the longitudinal extension direction of the medical object while the medical object is being moved relative to the reference unit by the mover device. The medical object may have different coefficients of friction along its longitudinal extension direction. The reference unit may be configured to detect and/or map the plurality of coefficients of friction as a function of the length of the medical object between the distal end portion and the introducer sheath and/or the mover device.

The processing unit may be configured to simulate the virtual frictional force as a function of the spatial positioning of the distal end portion of the medical object in the examination subject, the length of the medical object between the distal end portion and the introducer sheath and/or the mover device, and the plurality of coefficients of friction. The processing unit may for example be configured to simulate the virtual frictional force repeatedly in the event of a change in the spatial positioning of the distal end portion, for example as a result of a movement of the medical object by the mover device.

Embodiments provide a particularly precise simulation of the virtual frictional force between the hollow organ and the medical object. This provides the frictional force between the hollow organ and the medical object to be reliably identified or ruled out as the, for example sole, origin of the counterforce.

In an embodiment, the medical object, for example a distal end portion, may be disposed in a hollow organ of the examination subject. In the event of a counterforce being present, the processing unit may be configured to identify, on the basis of the dataset, an obstacle in the hollow organ at the distal end portion as the origin of the counterforce or, by ruling out the obstacle in the hollow organ on the basis of the dataset, to identify a frictional force between the hollow organ and the medical object as the origin of the counterforce.

The processing unit may be configured to determine the spatial positioning of the distal end portion of the medical object with respect to the dataset. The processing unit may be configured to identify an obstacle at the distal end portion of the medical object in the dataset, for example if a counterforce is present. The processing unit may for example be configured to identify a wall of the hollow organ, for example a vessel wall, and/or an occlusion, for example a thrombus, and/or a stenosis as the obstacle in the dataset. The processing unit may be configured to identify the obstacle on the basis of an image value and/or contrast value in the dataset. If the dataset contains a post-contrast image of the examination subject, for example of the hollow organ, the processing unit may be configured to identify the obstacle at the distal end portion of the medical object as a time-invariable structure in the hollow organ, for example on the basis of time intensity curves of image elements of the dataset.

The processing unit may be configured to identify the obstacle as a function of an operating parameter of the medical object and/or of the mover device, for example of a movement direction of the medical object. It may be provided that only such, for example time-invariable, structures in the hollow organ that adjoin the distal end portion of the medical object along the movement direction are identified as an obstacle. The processing unit may be configured to identify as an obstacle such structures in the hollow organ that impede and/or restrict the movement of the medical object. The processing unit may be configured to identify the obstacle in the hollow organ at the distal end portion of the medical object as the origin of the counterforce on the basis of the dataset.

The processing unit may be configured to rule out an obstacle at the distal end portion of the medical object, for example along the movement direction of the medical object, on the basis of the dataset. The processing unit may be configured to identify the frictional force between the medical object and the hollow organ as the, for example sole, origin of the counterforce by ruling out an obstacle in the hollow organ at the distal end portion of the medical object on the basis of the dataset.

The mover device may be configured to adjust a movement direction and/or movement speed of the medical object based on the signal, for example on the identified origin of the counterforce, in such a way that the counterforce is reduced. The mover device may be configured to move the medical object in such a way that the distal end portion of the medical object evades the obstacle identified in the hollow organ.

Embodiments provide a precise identification of the origin of the counterforce, for example without additional intraoperative imaging and/or radiation exposure of the examination subject. A risk of injury to the examination subject may be reduced as a result.

In an embodiment, the dataset may contain an image and/or a model of the examination subject and of the medical object at least partially disposed in the examination subject. The processing unit may be configured to determine the spatial positioning of the distal end portion of the medical object in the dataset.

The dataset may contain a two-dimensional and/or three-dimensional image of the examination subject, for example of the hollow organ, and the medical object at least partially disposed in the examination subject, for example in the hollow organ. The dataset may image the examination subject and the medical object in a time-resolved manner and/or intraoperatively, for example following the introduction of the medical object. The dataset may include a masked and/or segmented image of the hollow organ and/or of the medical object. For example, the dataset may have been acquired in accordance with a digital subtraction angiography (DSA) procedure. A contrast agent flow in the hollow organ and/or a movement of the medical object in the hollow organ may be imaged as a variation with time, for example during a fill phase of the DSA procedure.

The dataset may contain an, for example two-dimensional and/or three-dimensional, model of the examination subject, for example of the hollow organ, and/or of the medical object. The dataset may for example include a model of the medical object, for example a line model and/or a volume mesh model, that may be generated and/or received and/or selected from a selection of a plurality of models of different medical objects as a function of the parameter of the medical object, for example a material parameter and/or an operating parameter. Alternatively, or in addition, the processing unit may be configured to generate the model of the examination subject, for example of the hollow organ, and/or the model of the medical object based on an image, for example by segmentation. The medical object may include a marker structure, for example at the distal end portion, that provides for the medical object in the hollow organ to be identified and/or localized in the dataset.

The processing unit may be configured to determine the spatial positioning of the distal end portion of the medical object in the, for example intraoperative, dataset. This may be realized for example by registration of the dataset with the coordinate system of the examination subject. The processing unit may be configured to determine a spatial trajectory of the medical object, for example between the introducer sheath and the distal end portion, in the dataset.

For example, the mover device may be configured to continue the movement of the medical object in the presence of a counterforce when an obstacle at the distal end portion has been ruled out on the basis of the, for example intraoperative, dataset. This may reduce a risk of injury to structures, for example to the hollow organ, due to a movement of the medical object.

Embodiment provides for the spatial positioning of the distal end portion of the medical object in the examination subject to be determined in a precise manner. The simulation of the virtual frictional force and/or the identification of the origin of the counterforce may be improved. This is made possible for example as a result of determining the spatial trajectory of the medical object in the examination subject, for example in the hollow organ, on the basis of the dataset.

In an embodiment, the medical object, for example a distal end portion, may be disposed in a hollow organ of the examination subject. The processing unit may be configured to identify, given the presence of a counterforce, a meandering and/or a spiraling of the medical object in the hollow organ on the basis of the dataset. The mover device may be configured to move the medical object in addition as a function of the identified meandering and/or spiraling of the medical object in the hollow organ.

The processing unit may be configured to identify the meandering and/or spiraling of the medical object in the hollow organ on the basis of the dataset, for example on the basis of the spatial trajectory of the medical object imaged therein. The meandering of the medical object describes for example a winding course of the medical object, the winding course following a flexion, for example a curve, of the hollow organ mostly on an outer side of the curve of the hollow organ. A rotation of the medical object by the mover device may result in a spiraling of the medical object. The spatial trajectory of the medical object in the hollow organ may describe an at least partially spiral-shaped, for example spatially twisted, course. The processing unit may be configured to identify the meandering and/or spiraling of the medical object on the basis of the two-dimensional and/or three-dimensional image of the spatial trajectory of the medical object in the dataset.

Alternatively, or in addition, the processing unit may be configured to identify the meandering and/or spiraling of the medical object by determining a deviation in the dataset between a predefined and an actual spatial positioning of the distal end portion of the medical object. For example, the meandering and/or spiraling of the medical object in the hollow organ may cause a shortening of an effective length of the medical object between the distal end portion and the introducer sheath and/or the mover device.

The meandering and/or spiraling may be caused by an obstacle along the movement direction of the medical object and/or by the frictional force between the hollow organ and the medical object. For example, the meandering and/or spiraling of the medical object in the hollow organ may lead to an increase in the size of a contact area between the medical object and the hollow organ. This may result in an increase in the frictional force between the medical object and the hollow organ and consequently to an increase in the counterforce.

The processing unit may be configured to simulate the virtual frictional force in addition based on the identified meandering and/or spiraling of the medical object in the hollow organ. The mover device may be configured to adjust the movement of the medical object, for example a movement direction and/or movement speed, in addition as a function of the identified meandering and/or spiraling of the medical object in the hollow organ in such a way that the counterforce is reduced.

Embodiments provide an improved simulation of the virtual frictional force. An improved adjustment of the movement of the medical object by the mover device may be made possible by the identification of the meandering and/or spiraling of the medical object in the hollow organ. A risk of injury to structures, for example to the hollow organ, due to a movement of the medical object may be reduced as a result.

In an embodiment, the device may additionally include a renewal unit. The renewal unit may be configured to renew a surface of the medical object, at least in sections, as a function of the signal in such a way that a coefficient of friction of the surface is reduced.

The renewal unit may be configured for example to hydrophilize and/or hydrophobize the surface of the medical object. For example, the renewal unit may be configured to hydrophilize the surface of the medical object by, for example local, application of a plasma. Alternatively, or in addition, the renewal unit may be configured to hydrophilize and/or hydrophobize by applying a substance, for example a coating, onto the surface of the medical object. It may be advantageous, depending on the field of application of the medical object in the examination subject, to hydrophilize or hydrophobize the surface of the medical object.

At the same time, the renewal unit may be configured to deposit the substance in powder form, for example, for example by applying an electrostatic field between the surface of the medical object and the renewal unit, and/or in gaseous form and/or in liquid form. The renewal unit may be configured to fix the substance, for example by applying a substance and/or by applying a form of electromagnetic radiation, for example light, and/or by thermal action on the surface of the medical object.

Alternatively, or in addition, the renewal unit may be configured to renew the surface of the medical object by removing a predefined layer of the surface of the medical object. The medical object may have at its surface, for example, a plurality of hydrophilic and/or hydrophobic layers, for example arranged one above the other, that are mechanically and/or chemically and/or electromagnetically strippable.

The renewal unit may be configured to renew the surface of the medical object in such a way that the coefficient of friction of the renewed surface is reduced. The renewal unit may be configured for example to renew the surface of the medical object at least in sections, for example at the distal end portion and/or between the distal end portion and the introducer sheath and/or between the distal end portion and the mover device.

Embodiments provide the frictional force between medical object and hollow organ to be reduced, as a result of which the counterforce may be reduced. This also enables the force required to move the medical object, that the mover device transmits to the medical object, to be reduced. A risk of damage to structures of the medical object due to a movement of the medical object may be reduced as a result. An inclination of the medical object to meander and/or to form a spiral in the hollow organ may be reduced by reducing the coefficient of friction by the renewal unit.

In an embodiment, the renewal unit may be disposed on the mover device and/or on an introducer sheath for introducing the medical object into the examination subject. The mover device may be configured to move the medical object at least partially out of the examination subject as a function of the signal. The renewal unit may be configured to renew the surface of the moved-out section of the medical object.

For example, the renewal unit may be integrated at least partially into the introducer sheath and/or the mover device, for example the cassette element. It is possible to affect a movement of the medical object relative to the renewal unit when a movement, for example a translation and/or rotation, is initiated by the mover device. The renewal unit may for example be arranged annularly and/or at least in sections around the medical object.

The renewal unit may be configured to renew the surface of the medical object, for example along the longitudinal extension direction of the medical object. Alternatively, or in addition, the renewal unit may be disposed as movable, for example translationally and/or rotationally, in relation to the medical object and/or the mover unit and/or the introducer sheath. This provides a maximally comprehensive renewal of the surface of the medical object to be achieved by the renewal unit.

The mover device may be configured to move the medical object at least partially, for example completely, out of the examination subject as a function of the signal, for example if a counterforce is present and/or if the frictional force between medical object and hollow organ is identified as the, for example sole, origin of the counterforce. The moved-out section may be moved relative to the renewal unit, for example while the medical object is being moved out by the mover device. The renewal unit may be configured to renew the surface of the moved-out section of the medical object. Once renewal of the surface of the moved-out section of the medical object by the renewal unit has been completed, the mover device may be configured to reposition the medical object, for example at the original positioning of the distal end portion before the moving-out action, in the examination subject, for example in the hollow organ.

Embodiments provide a particularly flexible implementation of the renewal unit. The renewal unit may be configured for renewing different medical objects. The moving out, renewing of the surface of the medical object and subsequent repositioning of the at least one part of the medical object may result in a reduction of a previously existing meandering and/or spiraling of the medical object in the hollow organ. The renewal of the surface of the medical object by the renewal unit may lead to a reduction in the coefficient of friction of the surface of the medical object, as a result of which an inclination of the medical object to meander and/or form a spiral in the hollow organ may be reduced.

In an embodiment, the renewal unit may be at least partially integrated into the medical object. The renewal unit may be configured to renew the surface of the medical object at least on a section-by-section basis while the section to be renewed is disposed in the examination subject.

The renewal unit may be disposed as movable, for example translationally and/or rotationally, in relation to the section to be renewed, for example to the distal end portion, of the medical object. The renewal unit may for example be arranged annularly and/or at least in sections around the section to be renewed. The renewal unit may be configured to renew the surface of the section to be renewed, for example of the distal end portion, of the medical object in which the renewal unit is moved along the section to be renewed, for example by a Bowden cable.

Alternatively, or in addition, at least one section, for example the distal end portion, of the medical object may be movable, for example translationally and/or rotationally, in relation to the renewal unit. The renewal unit may be fixedly disposed on the medical object. For example, the at least one section, for example the distal end portion, may be drivable into the renewal unit. The renewal unit may be configured to renew the surface of the driven-in section, for example the distal end portion, of the medical object.

Embodiments provide the surface of the section of the medical object to be renewed, for example while the section to be renewed is disposed in the hollow organ. This permits a particularly time-efficient renewal of the surface and consequently a reduction in the coefficient of friction, thus providing a repositioning of the distal end portion by the mover device, for the purpose of renewing its surface by the renewal unit, to be minimized.

Embodiments provide a system including a device for moving a medical object and to a medical imaging device. In this regard the medical imaging device is configured to acquire a dataset of the examination subject and provide the dataset to the processing unit.

The system substantially corresponds to the features of the device for moving a medical object. Features, advantages or alternative embodiments mentioned in this context may equally be applied also to the other claimed subject matters, and vice versa.

The dataset and/or the examination subject and/or the device may for example possess all the characteristics and features that have been described in relation to the device for moving a medical object, and vice versa.

The medical imaging device may be configured for example as a magnetic resonance tomography (MRT) system and/or a computed tomography (CT) system and/or an ultrasound device and/or a medical x-ray device, for example a medical C-arm x-ray device. The medical imaging device may be configured for acquiring the dataset of the examination subject, for example preoperatively and/or intraoperatively. For example, the medical imaging device may be configured to acquire the dataset containing an image of the examination subject, for example of the hollow organ, and/or of the medical object, for example of the distal end portion.

The medical imaging device may be configured to provide the dataset to the device. The providing may for example include storing the dataset on a computer-readable storage medium and/or displaying the same on a visualization unit and/or transferring the same to the processing unit.

Embodiments provide a particularly precise movement of the medical object, for example a reduction in a risk of injury to the examination subject during a movement of the medical object by the mover device.

Embodiments provide a method for providing a signal. A moving and/or holding of a medical object by a mover device has taken place prior to commencement of the method. The mover device is configured to hold and/or move the medical object at least partially disposed in the mover device by transmission of a force. The medical object is disposed at least partially in an examination subject. In a first step a) of the method, a sensor signal of a sensor unit is received. The sensor unit is configured to detect a counterforce exerted by the medical object on the mover device and acting in the opposite direction to the force. The sensor signal contains information relating to the counterforce. In a second step b), a dataset is received, the dataset containing an image of the examination subject. In a third step c), a spatial positioning of a distal end portion of the medical object is determined with respect to the dataset. Furthermore, in a fourth step d), an origin of the counterforce is identified on the basis of the sensor signal, the spatial positioning of the distal end portion and the dataset. In a fifth step e), the signal is provided as a function of the origin of the counterforce.

The method for providing a signal substantially corresponds to features of the device for moving a medical object. Features, advantages or alternative embodiments mentioned in this context may equally be applied also to the other claimed subject matters, and vice versa.

The mover device and/or the medical object and/or the examination subject and/or the sensor unit may for example possess all characteristics and features that have been described in relation to the device for moving a medical object, and vice versa.

The receiving of the sensor signal and/or of the dataset may include for example an acquisition thereof and/or readout thereof from a computer-readable data memory and/or a receiving thereof from a data storage unit, for example a database. The sensor signal may be provided by the sensor unit. The dataset may be provided by a medical imaging device for acquiring the dataset.

The counterforce may act in the opposite direction to the force for holding and/or moving, for example for translating and/or rotating, the medical object. The sensor unit may include a force transducer for detecting the counterforce. The sensor unit may be configured to provide the sensor signal as a function of the detected counterforce. The sensor signal may contain information relating to a direction and/or a magnitude of the counterforce. The sensor signal may be time-resolved. The sensor signal may additionally include an operating parameter of the mover device and/or an operating parameter of the medical object and/or a physiological parameter of the examination subject, for example as metadata. The sensor signal may map a period of time of the movement of the medical object by the mover device prior to commencement of the method.

The dataset may for example include all the characteristics and features that have been described in relation to the device for moving a medical object, and vice versa.

In step c), the spatial positioning, for example a spatial position and/or orientation, of the distal end portion of the medical object may be determined with respect to the dataset. A length of the medical object between the distal end portion of the medical object and an introducer sheath for introducing the medical object and/or the mover device, for example along the longitudinal extension direction of the medical object, may be determined based on an operating parameter of the mover device. The operating parameter of the mover device may include information relating to the movement of the medical object, for example a translation and/or rotation, that took place by the mover device prior to commencement of the method. A spatial trajectory of the medical object in the examination subject, for example in the hollow organ, may also be determined in step c) based on the dataset and the length of the medical object between the distal end portion of the medical object and the introducer sheath and/or the mover device.

A change in the spatial positioning of the distal end portion with respect to the dataset may additionally be determined in step c). The spatial positioning of the distal end portion, for example the determined change in the spatial positioning of the distal end portion, may be compared with a control default of the mover device, the control default containing information, for example an instruction, for moving the medical object, for example for positioning the distal end portion in the examination subject, prior to commencement of the method.

In step d), the origin of the counterforce may be identified as a function of the counterforce, for example a direction and/or a magnitude of the counterforce, of the spatial positioning of the distal end portion with respect to the dataset, and of the dataset. Identifying the origin of the counterforce may include identifying or ruling out the frictional force between the medical object and the examination subject, for example the hollow organ, as the, for example sole, origin of the counterforce.

If a change in the spatial positioning of the distal end portion of the medical object is determined in the presence of a counterforce, that change deviates from the control default of the mover device, the frictional force between the medical object and the hollow organ may be identified in step d) as the, for example sole, origin of the counterforce. If, on the other hand, no change in the spatial positioning of the distal end portion of the medical object is determined in the presence of a counterforce, the control default of the mover device including predefined a force for moving the medical object, the origin of the counterforce may be identified in addition on the basis of the dataset. An incorrect positioning, for example an incorrect orientation, of the distal end portion of the medical object in the hollow organ may be identified in step d) as the origin of the counterforce based on the, for example current, spatial positioning with respect to the dataset.

The providing of the signal may for example include storing the signal on a computer-readable storage medium and/or displaying the same on a visualization unit and/or transferring the same to the processing unit. For example, the signal may be provided to the mover device in step e). Alternatively, or in addition, the signal containing information relating to the counterforce and/or the origin of the counterforce may be displayed to the user by the visualization unit.

Embodiments provide an origin of the counterforce to be identified taking into account the, for example current, spatial positioning of the distal end portion of the medical object, the dataset and the detected counterforce.

In an embodiment, the medical object, for example the distal end portion, may be disposed in a hollow organ of the examination subject. Step c) may additionally include a step c.1), where an obstacle in the hollow organ at the distal end portion of the medical object is identified as the origin of the counterforce on the basis of the dataset. Alternatively, a frictional force between the hollow organ and the medical object may be identified as the origin of the counterforce by ruling out the obstacle in the hollow organ on the basis of the dataset.

In an embodiment of the method, the dataset may contain an image and/or a model of the examination subject and of the medical object at least partially disposed in the examination subject. The spatial positioning of the distal end portion of the medical object may also be determined in the dataset in step c).

In an embodiment, the medical object, for example the distal end portion, may be disposed in a hollow organ of the examination subject. Step c) may additionally include a step c.2), a meandering and/or a spiraling of the medical object in the hollow organ being identified in step c.2) on the basis of the dataset. The signal may be provided in step e) in addition as a function of the identified meandering and/or spiraling of the medical object in the hollow organ.

The meandering and/or spiraling of the medical object in the hollow organ may be identified on the basis of the spatial trajectory of the medical object imaged in the dataset. For example, the meandering and/or spiraling of the medical object may be identified on the basis of a two-dimensional and/or three-dimensional image of the spatial trajectory of the medical object in the hollow organ on the basis of the dataset.

Alternatively, or in addition, the meandering and/or spiraling of the medical object may be identified by determining a deviation in the dataset between a predefined and an actual spatial positioning of the distal end portion of the medical object. For example, the meandering and/or spiraling of the medical object in the hollow organ may cause an effective length of the medical object between the distal end portion and the introducer sheath to be shortened.

The meandering and/or spiraling of the medical object in the hollow organ may have caused an increase in the size of the contact area between the medical object and the hollow organ. The frictional force between the medical object and the hollow organ, and consequently the counterforce, may have been increased as a result. The signal containing information relating to the identified meandering and/or the identified spiraling of the medical object in the hollow organ may be provided in step e). This may permit a more precise identification of the origin of the counterforce, for example taking into account the spatial trajectory of the medical object in the hollow organ.

In an embodiment, the medical object, for example the distal end portion, may be disposed in a hollow organ of the examination subject. In this case step a) may additionally include steps a.1) and a.2), a reference signal of a reference unit being received in step a.1). The reference unit may be configured to detect at least one coefficient of friction of the medical object on the mover device and/or on an introducer sheath for introducing the medical object into the examination subject. In a step a.2), a virtual frictional force between the medical object and the hollow organ may be simulated on the basis of the at least one coefficient of friction. Step c) may include a step c.3), where a frictional force between the hollow organ and the medical object may be identified or ruled out as the origin of the counterforce in step c.3) based on a comparison between the sensor signal and the virtual frictional force.

In an embodiment, the reference unit may be configured to detect a plurality of coefficients of friction along a longitudinal extension direction of the medical object. A movement of the medical object relative to the reference unit by the mover device may have taken place prior to commencement of the method. The virtual frictional force may be simulated in step a.2) on the basis of the dataset and the plurality of coefficients of friction as a function of a spatial positioning of the distal end portion of the medical object in the examination subject.

The virtual frictional force may be simulated in addition based on the identified meandering and/or spiraling of the medical object in the hollow organ.

Embodiments provide a method for controlling a renewal unit. A signal is received by applying a method for providing a signal. The renewal unit is controlled as a function of the signal for the purpose of renewing a surface of the medical object in order to reduce a coefficient of friction of the surface.

The renewal unit may for example possess all the characteristics and features that have been described in relation to the device for moving a medical object, and vice versa. The advantages of the method for controlling a renewal unit substantially correspond to the advantages of the device for moving a medical object and/or of the method for providing a signal. Features, advantages or alternative embodiments mentioned in this context may equally be applied also to the other claimed subject matters, and vice versa.

Embodiments provide a computer program product including a computer program that may be loaded directly into a memory of a processing unit, having program sections for performing all steps of the method for providing a signal and/or of a method for controlling a renewal unit when the program sections are executed by the processing unit. The computer program product may in this case include a piece of software including source code that still requires to be compiled and linked or that only needs to be interpreted, or an executable software code that has only to be loaded into the processing unit in order to execute. The computer program product provides the method for providing a signal and/or the method for controlling a renewal unit by a processing unit to be performed quickly and in an identically repeatable and robust manner. The computer program product is configured in such a way that it is able to carry out the method steps by the processing unit.

The computer program product is stored for example on a computer-readable storage medium or held resident on a network or server, from where it may be loaded into the processor of a processing unit that is directly connected to the processing unit or that may be configured as part of the processing unit. Control information of the computer program product may also be stored on an electronically readable data medium. The control information of the electronically readable data medium may be configured in such a way that it performs an inventive method when the data medium is used in a processing unit. Examples of electronically readable data media are a DVD, a magnetic tape or a USB stick on which electronically readable control information, for example software, is stored. When the control information is read from the data medium and loaded into a processing unit, all inventive embodiments of the above-described methods may be performed.

Embodiments provide a computer-readable storage medium and/or electronically readable data medium on which program sections that may be read and executed by a processing unit are stored in order to perform all the steps of the method for providing a signal and/or for controlling a renewal unit when the program sections are executed by the processing unit.

A largely software-based implementation includes the advantage that processing units already used previously in the prior art may also be easily upgraded by a software update in order to operate according to the invention. In addition to the computer program, such a computer program product may, where appropriate, include additional constituent parts such as e.g., a set of documentation and/or additional components, as well as hardware components, such as e.g., hardware keys (dongles, etc.) to provide use of the software.

BRIEF DESCRIPTION OF THE FIGURES

Embodiments are illustrated in the drawings and are described in more detail below. The same reference signs are used for like features in different figures.

DETAILED DESCRIPTION

Figure 1:
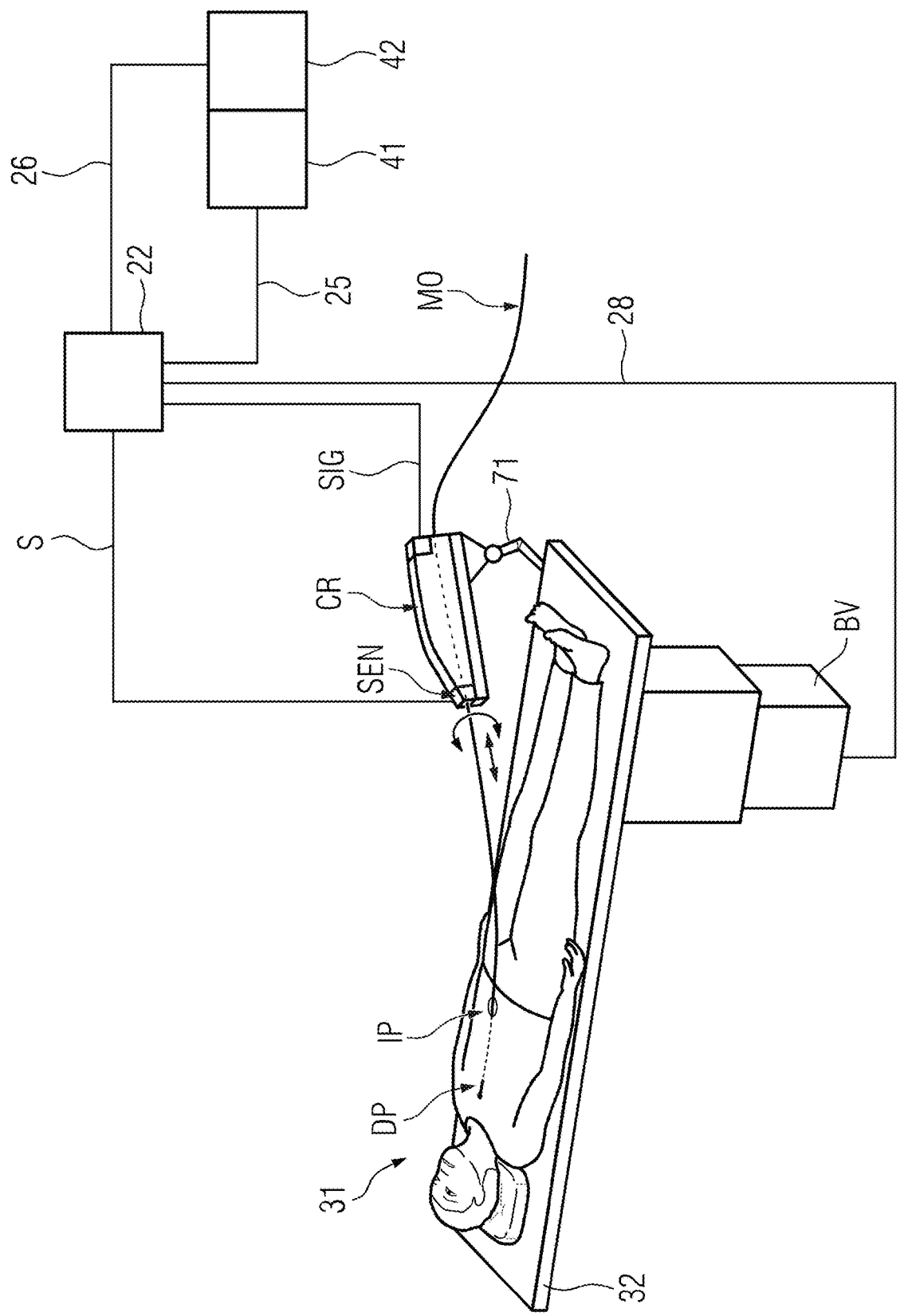
FIG. 1 depicts a schematic view of a device for moving a medical object according to an embodiment.

FIG. 1 depicts a schematic view of a device for moving a medical object. The device may include a mover device CR that is configured to hold and/or move the medical object MO at least partially disposed in the mover device CR by transmitting a force.

The mover device CR may be configured for example as a catheter robot, for example to allow remote manipulation of the medical object MO. The medical object MO may be configured as an, for example elongate, surgical and/or diagnostic instrument. For example, the medical object MO may be rigid and/or flexible and/or mechanically deformable at least in sections. The medical object MO may be configured for example as a catheter and/or endoscope and/or guidewire. The medical object MO may be introduced by way of an introducer sheath IP at an entry point or port into an examination subject 31 disposed on the patient support and positioning device 32, for example into a hollow organ of the examination subject 31. The patient support and positioning device 32 may be at least partially movable. For this purpose, the patient support and positioning device 32 may include a mover device BV, which mover device BV is controllable by a movement signal 28 from a processing unit 22.

The medical object MO may also have a distal end portion DP. The distal end portion DP may for example describe a tip and/or a section having a marker structure on the medical object MO. The distal end portion DP of the medical object MO may be disposed at least partially in the examination subject 31, for example in the hollow organ. The hollow organ may be for example a vessel section in which the distal end portion DP is at least partially disposed.

The mover device CR may be secured, for example so as to be movable, by a securing element 71, for example a stand and/or a robotic arm, to the patient support and positioning device 32. Advantageously, the mover device CR may be configured to move the medical object MO at least partially disposed therein translationally at least along a longitudinal extension direction of the medical object MO. The mover device CR may be configured to rotate the medical object MO around its longitudinal extension direction. Alternatively, or in addition, the mover device CR may be configured to control a movement of at least a part of the medical object MO, for example the distal end portion DP, for example the tip, of the medical object MO. The mover device CR may be configured to deform the distal end portion DP of the medical object MO in a defined manner, for example via a Bowden cable inside the medical object MO. The mover device CR may be controllable by a signal SIG from the processing unit 22.

The device may include a sensor unit SEN, the sensor unit SEN configured to detect a counterforce exerted by the medical object MO on the mover device CR and acting in the opposite direction to the force. The sensor unit SEN may include a force transducer that is configured to detect the counterforce exerted by the medical object MO on the force transducer. The sensor unit SEN may for example include an electromagnetic, for example capacitive and/or resistive and/or piezoelectric and/or electrodynamic, and/or mechanical and/or optical force transducer. The counterforce may act in the opposite direction to the force for holding and/or moving, for example for translating and/or rotating, the medical object MO. The sensor unit SEN, for example the force transducer, may be configured to provide a sensor signal S as a function of the detected counterforce. The sensor signal S may include information relating to a direction and/or a magnitude of the counterforce. The sensor signal may also be time-resolved. The sensor signal S may additionally include an operating parameter of the mover device CR and/or an operating parameter of the medical object MO and/or a physiological parameter of the examination subject 31, for example as metadata.

The sensor unit SEN may be disposed at least partially integrated into the mover device CR. The sensor unit SEN may be configured to provide the sensor signal S to the processing unit 22. The device, for example the processing unit 22, may be configured to provide the signal SIG as a function of the counterforce, for example as a function of the sensor signal S. For example, the device may be configured to provide the sensor signal S as the signal SIG. The signal SIG may include information relating to a direction and/or a magnitude of the counterforce.

The mover device CR may be configured to move the medical object MO as a function of the signal SIG. For this purpose, the processing unit 22 may be configured to compare the signal SIG with a predefined threshold value. In the event of the threshold value being exceeded by the signal SIG, the mover device CR may be configured to adjust the, for example current, movement of the medical object MO as a function of the signal SIG. For example, the mover device CR may be configured to stop an, for example current, movement of the medical object MO if a counterforce is detected by the sensor unit SEN. Alternatively or in addition, the mover device CR may be configured to adjust the, for example current, movement of the medical object MO as a function of the signal SIG if a counterforce is detected by the sensor unit SEN. For example, the mover device CR may be configured to move the medical object MO as a function of the signal SIG in such a way that the counterforce is reduced. For example, the mover device CR may be configured to adjust a movement direction and/or movement speed of the movement of the medical object MO as a function of the signal SIG. The mover device CR may be configured to control an at least section-wise deformation of the medical object MO, for example of the distal end portion DP, as a function of the signal SIG.

The device may include an input unit 42 that is configured to register an input by a user. The input unit 42 may for example include a keyboard and/or a pointing device, for example a computer mouse. The input by the user on the input unit 42 may permit an, for example supplementary, control of the device, for example of the mover device CR, and/or of a system and/or of the patient support and positioning device 32. For this purpose, the input element 42 may for example send an input signal 26 to the processing unit 22.

The device may include a visualization unit 41, for example a monitor and/or a display. The input unit 42 may be integrated at least partially into the visualization unit 41, for example in the case of a capacitive and/or resistive input display. The visualization unit 41 may be configured to display information and/or graphical representations of information of the device, for example of the mover device CR, and/or of the system. The processing unit 22 may for example send a visualization signal 25 to the visualization unit 41. For example, the visualization unit 41 may be configured to display a graphical representation of the signal SIG and/or information relating to the detected counterforce.

The processing unit 22 may be configured to receive an, for example preoperatively acquired, dataset. The dataset may contain an, for example preoperative, image of the examination subject 31. The processing unit 22 may be configured to determine a spatial positioning of the distal end portion DP of the medical object MO with respect to the dataset. The processing unit 22 may be configured to identify an origin of the counterforce as a function of the counterforce, for example a magnitude and/or a direction of the counterforce, of the spatial positioning of the distal end portion DP, and of the dataset. The processing unit 22 may be configured to provide the signal SIG as a function of the origin of the counterforce.

The processing unit 22 may be configured to identify, in the presence of a counterforce, an obstacle in the hollow organ at the distal end portion DP as the origin of the counterforce on the basis of the dataset or, by ruling out the obstacle in the hollow organ on the basis of the dataset, to identify a frictional force between the hollow organ and the medical object MO as the origin of the counterforce.

Figure 2:
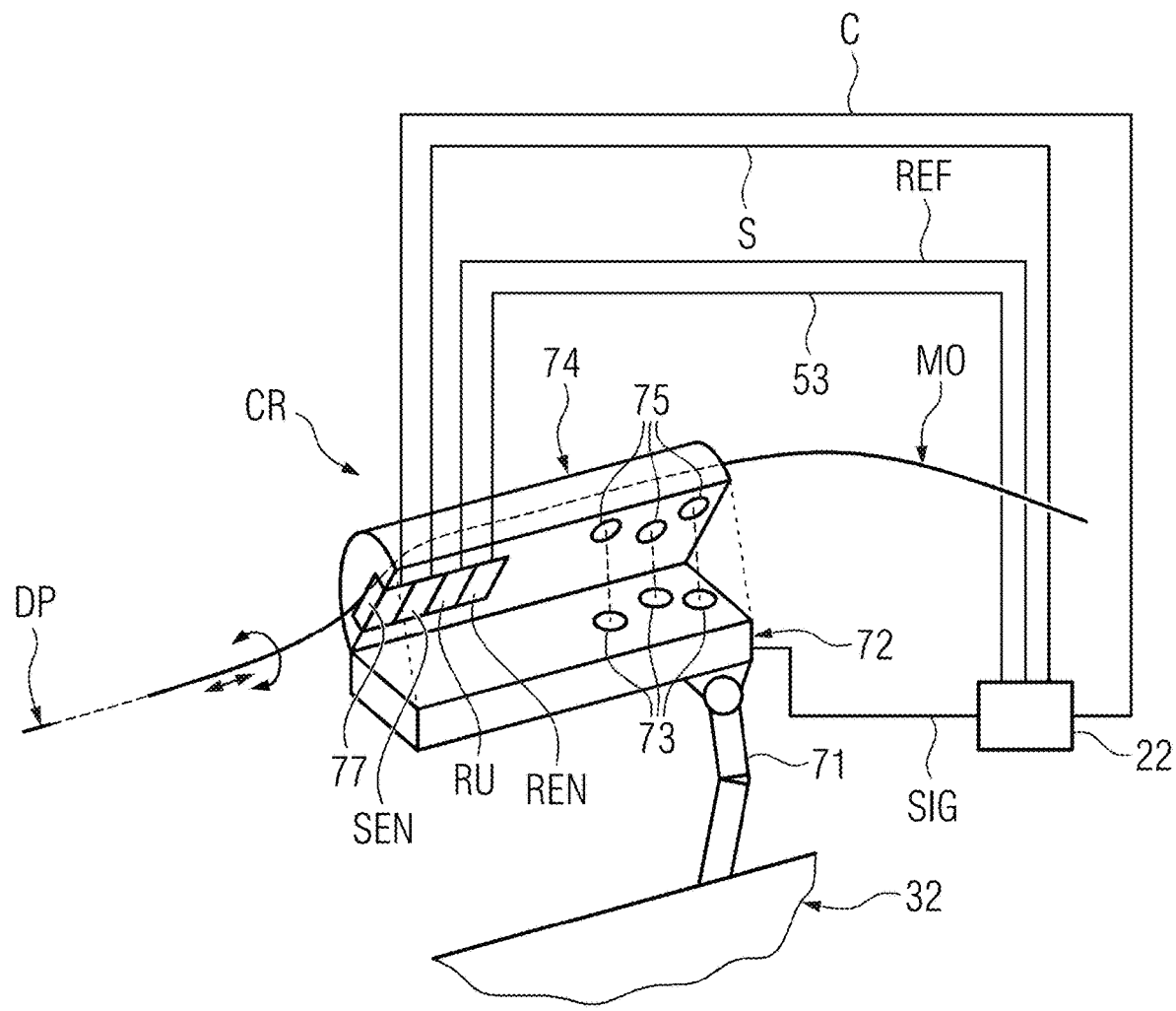
FIG. 2 depicts a schematic view of a mover device according to an embodiment.

FIG. 2 depicts a schematic view of the mover device CR for robotically moving the medical object MO. The mover device CR may include an, for example movable and/or displaceable, securing element 71. The mover device CR may include a cassette element 74 that is configured to accommodate at least a part of the medical object MO. The mover device CR may include a mover element 72 that is fixedly mounted to the securing element 71, for example a stand and/or a robotic arm. The securing element 71 may be configured to secure the mover element 72 to the patient support and positioning device 32, for example so as to be movable. The mover element 72 may include at least one, for example three, actuator element(s) 73, for example an electric motor, the processing unit 22 configured to control the at least one actuator element 73, for example by the signal SIG. The cassette element 74 may be couplable, for example mechanically and/or electromagnetically and/or pneumatically, to the mover element 72, for example to the at least one actuator element 73. The cassette element 74 may include at least one transmission element 75 that is movable as a result of the coupling between the cassette element 74 and the mover element 72, for example the at least one actuator element 73. For example, the at least one transmission element 75 may be movably coupled to the at least one actuator element 73. The transmission element 75 may be configured to transmit a movement of the actuator element 73 to the medical object MO in such a way that the medical object MO is moved along a longitudinal extension direction of the medical object MO and/or that the medical object MO is rotated around the longitudinal extension direction. The at least one transmission element 75 may include for example a roller and/or drum and/or shield and/or shearing plate.

The mover element 72 may include a plurality of, for example independently controllable, actuator elements 73. The cassette element 74 may include a plurality of transmission elements 75, for example at least one movably coupled transmission element 75 for each of the actuator elements 73. This may facilitate an, for example independent and/or simultaneous, movement of the medical object MO along different degrees of freedom.

The mover device CR, for example the at least one actuator element 73, may be controllable by the signal SIG from the processing unit 22. The movement of the medical object MO may be controlled, for example indirectly, by the processing unit 22. An orientation and/or position of the mover device CR relative to the examination subject 31 may be adjustable by a movement of the securing element 71.

The mover device CR may include a motion detection unit 77 that is configured to detect a relative movement of the medical object MO relative to the mover device CR. The motion detection unit 77 may include for example an encoder, for example a wheel encoder and/or a roller encoder, and/or an optical sensor, for example a barcode scanner and/or a laser scanner and/or a camera, and/or an electromagnetic sensor. The motion detection unit 77 may be configured to detect the relative movement of the medical object MO, for example by detecting the medical object MO relative to the mover device CR. Alternatively or in addition, the motion detection unit 77 may be configured to detect a movement and/or change in position of components of the mover device CR, which components are movably coupled to the medical object MO, for example the at least one actuator element 73 and/or the at least one transmission element 74. The motion detection unit 77 may be configured to provide a detection signal C to the processing unit 22 as a function of the detected relative movement of the medical object MO.

The sensor unit SEN and/or the motion detection unit 77 may be disposed at least partially integrated into the at least one actuator element 73 and/or the transmission element 75.

The device may include a reference unit RU, the reference unit RU configured to detect at least one coefficient of friction of the medical object MO on the mover device CR and/or on the introducer sheath IP for introducing the medical object MO into the examination subject 31. The reference unit RU may be disposed for example at least partially integrated into the mover device CR. The reference unit RU may be configured to provide the at least one coefficient of friction of the medical object MO to the processing unit 22 by a reference signal REF. The processing unit 22 may be configured to simulate a virtual frictional force between the medical object MO and the hollow organ on the basis of the at least one coefficient of friction, for example of the reference signal REF. The processing unit 22 may be configured to identify or rule out a frictional force between the hollow organ and the medical object MO as the origin of the counterforce based on a comparison between the counterforce and the virtual frictional force. In addition, the processing unit 22 may be configured to provide the signal SIG as a function of the origin of the counterforce.

The reference unit RU may additionally be configured to detect a plurality of coefficients of friction along a longitudinal extension direction of the medical object MO. The medical object MO may be movable relative to the reference unit RU by the mover device CR. The processing unit 22 may be configured to simulate the virtual frictional force as a function of the spatial positioning of the distal end portion DP of the medical object MO in the examination subject 31 and the plurality of coefficients of friction.

The device may include a renewal unit REN, the renewal unit REN being configured to renew a surface of the medical object MO as a function of the signal SIG at least in such a way that a coefficient of friction of the surface is reduced. For this purpose, the processing unit may send a renewal signal 53 to the renewal unit REN as a function of the signal SIG. In the embodiment depicted in FIG. 2, the renewal unit REN may be disposed at least partially integrated on the mover device CR. The mover device CR may be configured to move the medical object MO at least partially out of the examination subject 31 as a function of the signal SIG. The renewal unit REN may be configured to renew the surface of the moved-out section of the medical object MO.

Alternatively, or in addition, the renewal unit REN may be at least partially integrated into the medical object MO (not shown here). The renewal unit REN may be configured to renew the surface of the medical object MO, at least on a section-by-section basis, while the section to be renewed is disposed in the examination subject 31.

Figure 3:
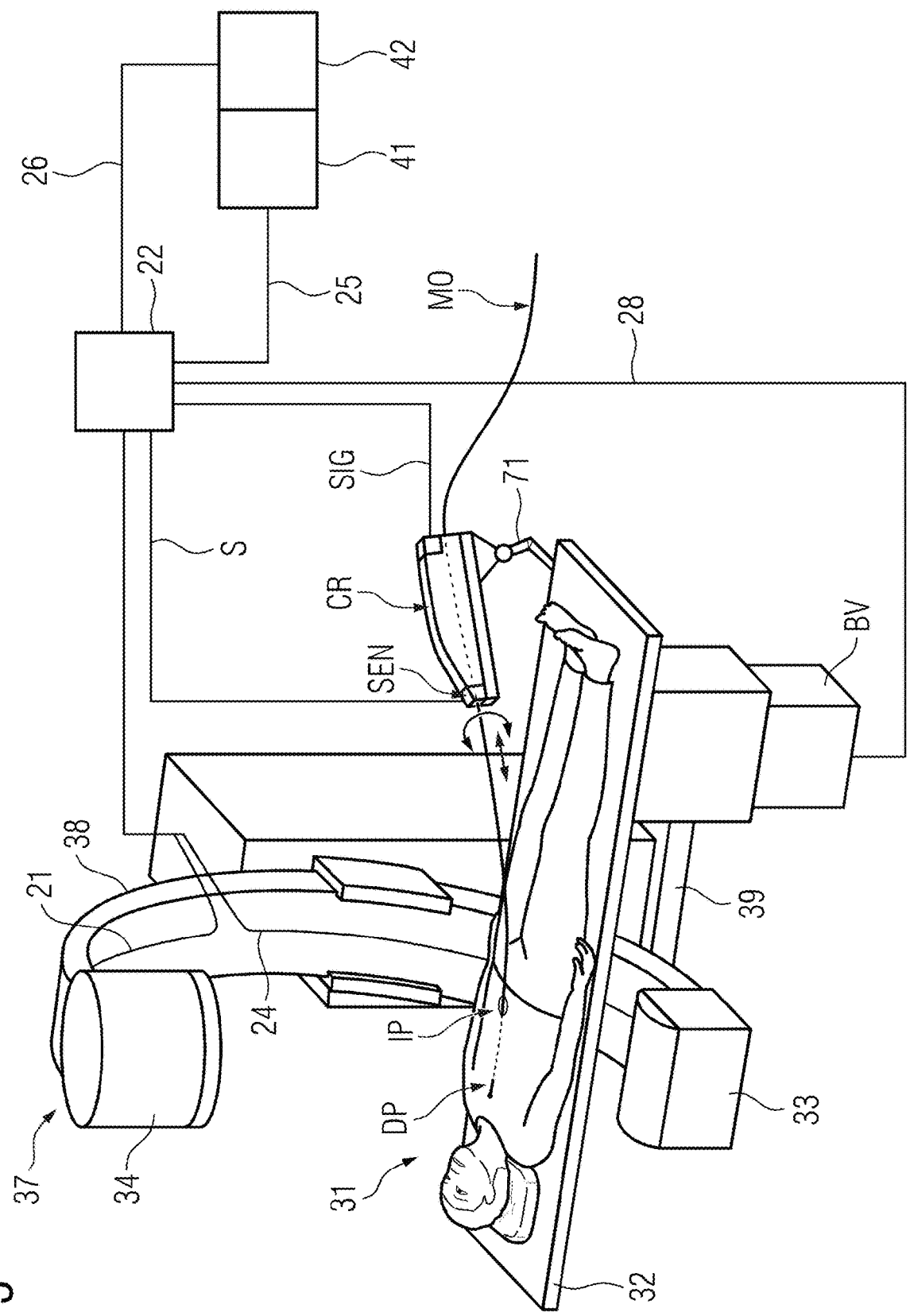
FIG. 3 depicts a schematic view of a system according to an embodiment.

FIG. 3 depicts a schematic view of a system, the system including a device for moving a medical object MO and a medical C-arm x-ray device 37, serving as an example of a medical imaging device. The medical C-arm x-ray device 37 may be configured for the, for example preoperative and/or intraoperative, acquisition of the dataset of the examination subject 31.

The medical C-arm x-ray device 37 may include a detector 34, for example an x-ray detector, and an x-ray source 33. In order to acquire the dataset, the arm 38 of the medical C-arm x-ray device 37 may be mounted so as to be movable around one or more axes. The medical C-arm x-ray device 37 may include a mover device 39 that allows the medical C-arm x-ray device 37 to move in space. The detector 34 and the x-ray source 33 may be movably mounted in a defined arrangement on a common C-arm 38.

The processing unit 22 may be configured to control a positioning of the medical C-arm x-ray device 37 relative to the examination subject 31 in such a way that the distal end portion DP of the medical object MO is imaged in the dataset acquired by the medical C-arm x-ray device 37. The positioning of the medical C-arm x-ray device 37 relative to the examination subject 31 may for example include a positioning of the defined arrangement of x-ray source 33 and detector 34, for example of the C-arm 38, around one or more spatial axes. The medical C-arm x-ray device 37 may include a mover device 39, for example a wheel system and/or a rail system and/or a robotic arm that allows the medical C-arm x-ray device 37 to move in space.

In order to acquire the dataset of the examination subject 31, the processing unit 22 may send a signal 24 to the x-ray source 33. The x-ray source 33 may thereupon transmit an x-ray beam, for example a cone beam and/or fan beam and/or parallel beam. When the x-ray beam strikes a surface of the detector 34 following an interaction with the examination region of the examination subject 31 that is to be imaged, the detector 34 may send a signal 21 to the processing unit 22. On the basis of the signal 21, the processing unit 22 may for example receive and/or reconstruct the dataset. The visualization unit 41 may be configured to display a graphical representation of the dataset.

The dataset may contain an image and/or a model of the examination subject 31, for example of the hollow organ, and of the medical object MO at least partially disposed in the examination subject 31. The processing unit 22 may be configured to determine the spatial positioning of the distal end portion DP in the dataset.

The processing unit 22 may be configured to identify, in the event of the counterforce being present, a meandering and/or spiraling of the medical object MO in the hollow organ on the basis of the dataset. The mover device CR may be configured to move the medical object MO in addition as a function of the identified meandering and/or spiraling of the medical object MO in the hollow organ.

Figure 4:
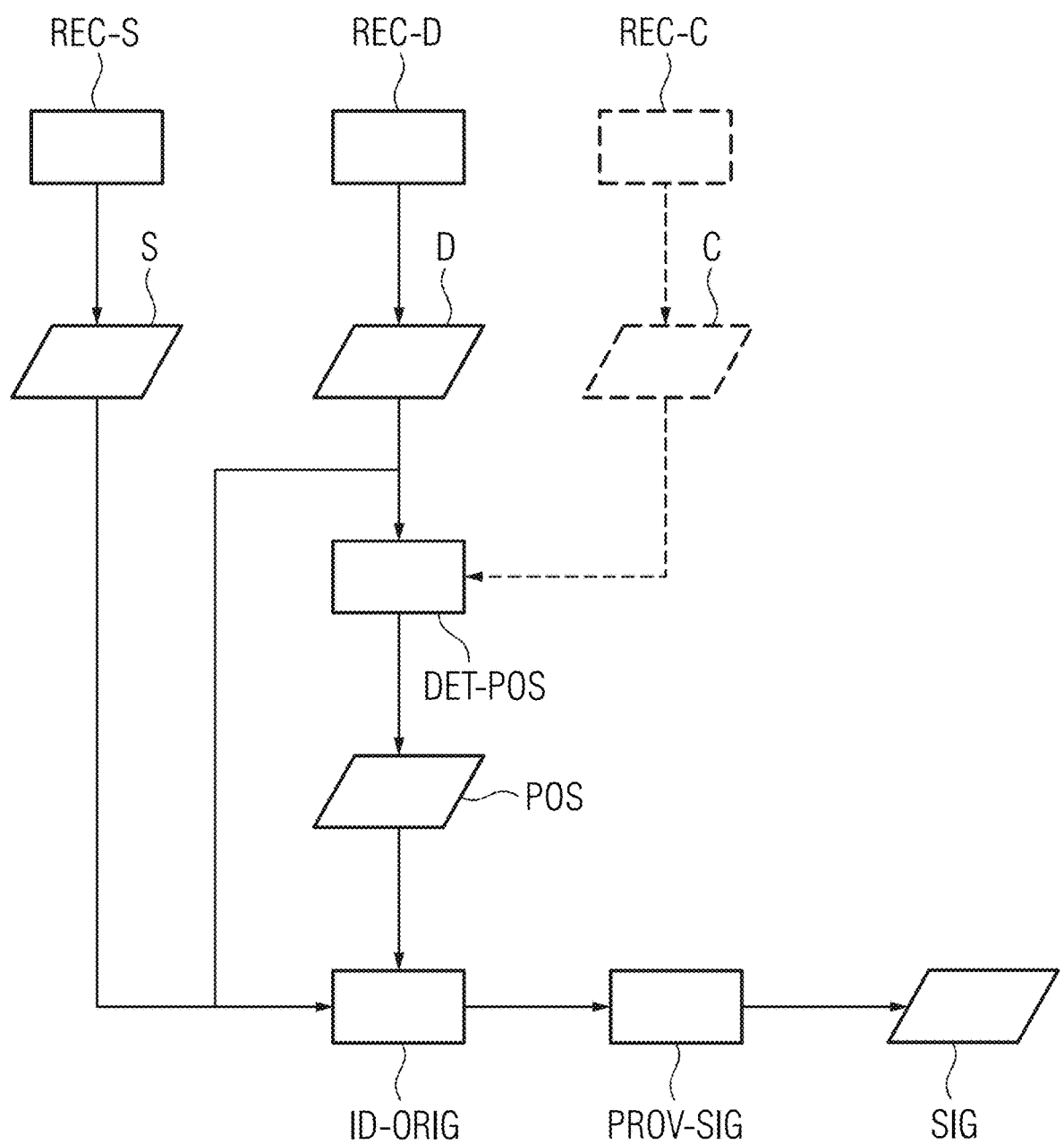
FIGS. 4 and 5 show schematic views of different embodiments of a method for providing a signal according to an embodiment.

FIG. 4 depicts a schematic view of an embodiment of a method for providing PROV-SIG a signal SIG. A moving and/or holding of the medical object MO by the mover device CR may have taken place prior to commencement of the method. In a first step a), the sensor signal S of the sensor unit SEN may be received REC-S. In a second step b), the, for example preoperative and/or intraoperative, dataset D may be received REC-D. In a third step c), the spatial positioning POS of the distal end portion DP of the medical object MO with respect to the dataset D may be determined DET-POS. For this purpose, the detection signal C may be received REC-C from the motion detection unit 77 and used, for example in addition. If the dataset D contains an image and/or a model of the examination subject 31 and of the medical object MO at least partially disposed in the examination subject 31, the spatial positioning POS of the distal end portion DP may be determined DET-POS in the dataset D. In a fourth step d), the origin of the counterforce may be identified ID-ORIG on the basis of the sensor signal S, the spatial positioning POS of the distal end portion DP and the dataset D. After this, the signal SIG may be provided PROV-SIG as a function of the origin of the counterforce.

Step c) may additionally include a step c.1), where either an obstacle in the hollow organ at the distal end portion DP may be identified in step c.1) as the origin of the counterforce on the basis of the dataset D or, by ruling out an obstacle in the hollow organ, a frictional force between the hollow organ and the medical object MO may be identified ID-ORIG as the origin of the counterforce.

In a step c.2), a meandering and/or spiraling of the medical object MO in the hollow organ may be identified on the basis of the dataset D. The signal SIG may be provided PROV-SIG in addition as a function of the identified meandering and/or spiraling of the medical object MO in the hollow organ.

Figure 5:
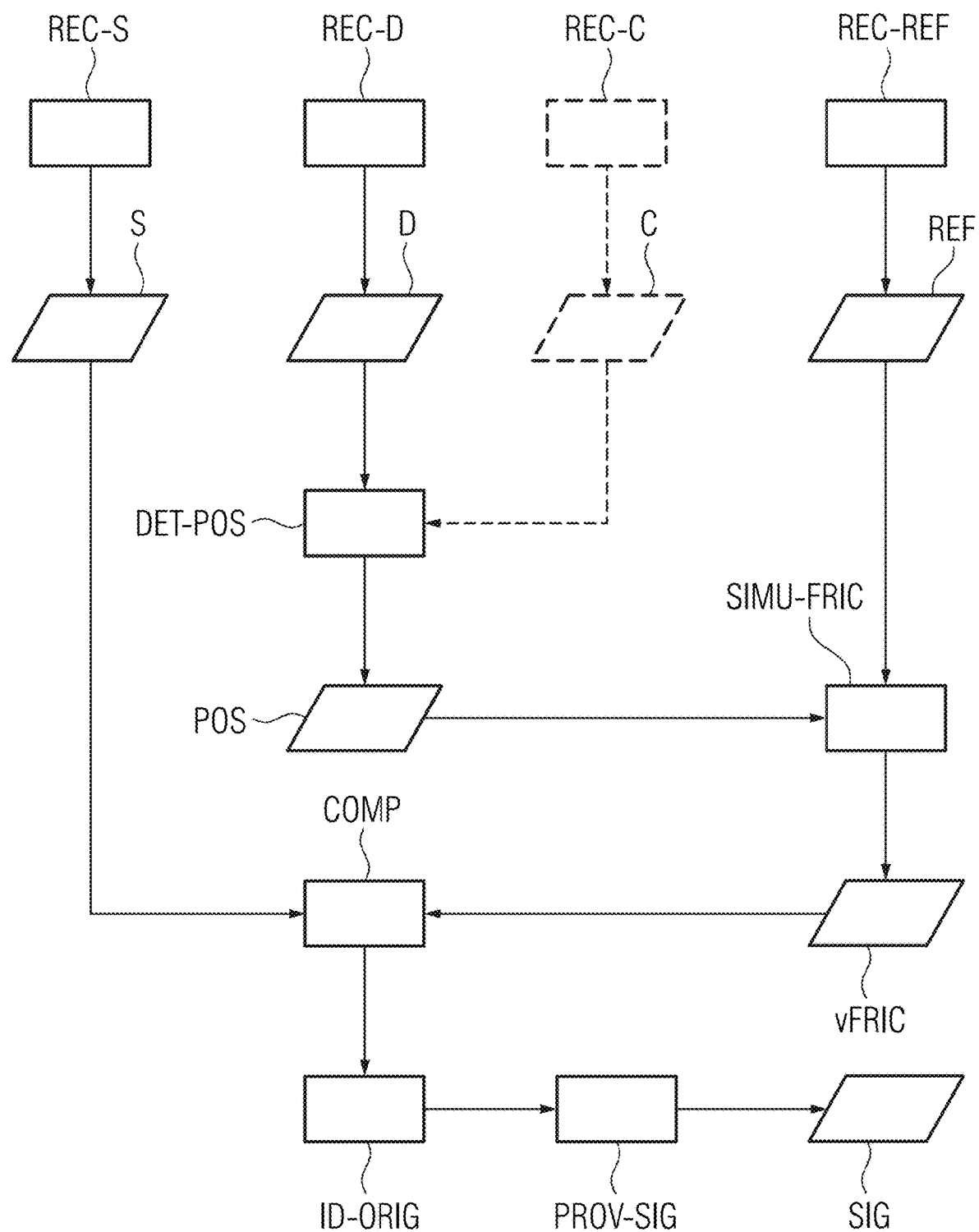

FIG. 5 schematically illustrates an embodiment of a method for providing PROV-SIG a signal SIG. Step a) may additionally include steps a.1) and a.2). In step a.1), the reference signal REF of the reference unit RU may be received REC-REF. Also, in step a.2), a virtual frictional force vFRIC between the medical object MO and the hollow organ may be simulated SIMU-FRIC on the basis of the at least one coefficient of friction, for example on the basis of the reference signal REF. Step c) may include a step c.3), where the frictional force between the medical object MO and the hollow organ may be identified or ruled out ID-ORIG based on a comparison COMP between the sensor signal S and the virtual frictional force vFRIC.

To the extent that the reference unit RU is configured to detect a plurality of coefficients of friction along the longitudinal extension direction of the medical object MO and a movement of the medical object MO relative to the reference unit RU by the mover device CR has taken place prior to commencement of the method, the virtual frictional force vFRIC may be simulated SIMU-FRIC on the basis of the dataset D and the plurality of coefficients of friction as a function of the spatial positioning POS of the distal end portion DP of the medical object MO in the examination subject 31.

Figure 6:
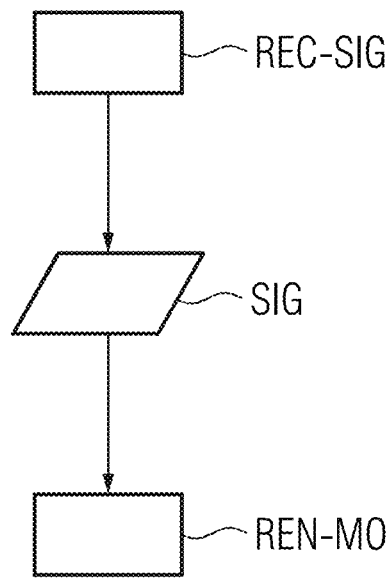
FIG. 6 depicts a schematic view of a method for controlling a renewal unit according to an embodiment.

FIG. 6 depicts a schematic view of a method for controlling a renewal unit REN. The signal SIG may be received REC-SIG by applying a method for providing a signal PROV-SIG. The renewal unit REN may be controlled as a function of the signal SIG for the purpose of renewing REN-MO the surface of the medical object MO in order to reduce the coefficient of friction of the surface.

The schematic illustrations contained in the described figures do not reflect a scale or proportions of any kind.

The methods described in detail in the foregoing, as well as the illustrated devices, are embodiments that may be modified in the most diverse ways by the person skilled in the art without leaving the scope of the invention. The use of the indefinite articles "a" or "an" does not exclude the possibility that the features in question may also be present more than once. Similarly, the terms "unit" and "element" do not rule out the possibility that the components in question consist of a plurality of cooperating subcomponents, that, if necessary, may also be distributed in space.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A device for moving a medical object, the device comprising:
   a mover device configured to hold, move, or hold and move the medical object at least partially disposed in the mover device by transmitting a force, wherein the medical object is disposed in a hollow organ of an examination subject; and
   a sensor unit configured to detect a counterforce exerted by the medical object on the mover device and acting in the opposite direction to the force;
   a reference unit comprising a sensor configured to detect at least one coefficient of friction of the medical object at the mover device and/or at an introducer sheath for introducing the medical object into the examination subject; and
   a processing unit configured to simulate a virtual frictional force between the medical object and the hollow organ on the basis of the at least one coefficient of friction and identify or rule out a frictional force between the hollow organ and the medical object as an origin of the counterforce based on a comparison between the counterforce and the virtual frictional force;
   wherein a signal is provided as a function of the counterforce,
   wherein the mover device is further configured to move the medical object as a function of the signal.

2. The device of claim 1, wherein the processing unit is further configured to:
   receive a dataset that contains an image of the examination subject;
   determine a spatial positioning of a distal end portion of the medical object with respect to the dataset;
   identify an origin of the counterforce as a function of the counterforce, the spatial positioning of the distal end portion and the dataset; and
   provide the signal as a function of the origin of the counterforce.

3. The device of claim 1, wherein the sensor of the reference unit is configured to detect a plurality of coefficients of friction along a longitudinal extension direction of the medical object;
- wherein the medical object is movable relative to the reference unit by the mover device; and
- wherein the processing unit is further configured to simulate a virtual frictional force as a function of a spatial positioning of a distal end portion of the medical object in the examination subject and the plurality of coefficients of friction.

4. The device of claim 2, wherein the processing unit is further configured, in an event of a counterforce being present, to:
- identify an obstacle in the hollow organ at the distal end portion as an origin of the counterforce on a basis of the dataset; or
- by ruling out the obstacle in the hollow organ on the basis of the dataset, identify a frictional force between the hollow organ and the medical object as the origin of the counterforce.

5. The device of claim 2, wherein the dataset contains an image, a model, or the image and the model of the examination subject and of the medical object at least partially disposed in the examination subject, wherein the processing unit is further configured to determine a spatial positioning of the distal end portion of the medical object in the dataset.

6. The device of claim 5, wherein the processing unit is further configured to identify, in the presence of a counterforce, a meandering, spiraling, or meandering and spiraling of the medical object in the hollow organ on the basis of the dataset; and
- wherein the mover device is further configured to move the medical object in addition as a function of the identified meandering, spiraling, or meandering and spiraling of the medical object in the hollow organ.

7. The device of claim 1, further comprising:
- a renewal unit configured to renew a surface of the medical object, at least in sections, as a function of the signal in such a way that a coefficient of friction of the surface is reduced.

8. The device of claim 7, wherein the renewal unit is disposed at the mover device and/or at an introducer sheath for introducing the medical object into the examination subject,
- wherein the mover device is configured to move the medical object at least partially out of the examination subject as a function of the signal, and
- wherein the renewal unit is configured to renew the surface of the moved-out section of the medical object.

9. The device of claim 7, wherein the renewal unit is at least partially integrated into the medical object and wherein the renewal unit is configured to renew the surface of the medical object, at least on a section-by-section basis, while the section to be renewed is disposed in the examination subject.

10. A method for providing a signal, the method comprising:
- moving, holding, or moving and holding of a medical object by a mover device by transmitting a force, wherein the medical object is disposed in a hollow organ of an examination subject;
- receiving a sensor signal of a sensor unit configured to detect a counterforce exerted by the medical object on the mover device and acting in the opposite direction to the force, wherein the sensor signal contains information relating to the counterforce;
- receiving a reference signal of a reference unit, wherein the reference unit comprises a sensor that is configured to detect at least one coefficient of friction of the medical object at the mover device and/or at an introducer sheath for introducing the medical object into the examination subject;
- simulating a virtual frictional force between the medical object and the hollow organ on the basis of the at least one coefficient of friction;
- receiving a dataset that contains an image of the examination subject;
- determining a spatial positioning of a distal end portion of the medical object with respect to the dataset;
- identifying an origin of the counterforce on a basis of the sensor signal, the spatial positioning of the distal end portion, the reference signal, the virtual signal, and the dataset; and
- providing the signal as a function of the origin of the counterforce.

11. The method of claim 10, wherein determining additionally comprises:
- identifying an obstacle in the hollow organ at the distal end portion as the origin of the counterforce on the basis of the dataset; and
- identifying a frictional force between the hollow organ and the medical object as the origin of the counterforce by ruling out the obstacle in the hollow organ on the basis of the dataset.

12. The method of claim 11, wherein the dataset further contains a model of the examination subject and of the medical object; wherein determining comprises determining the spatial positioning a distal end portion of the medical object in the dataset.

13. The method as claimed in claim 12, wherein determining additionally comprises:
- identifying a meandering, spiraling, or meandering and spiraling of the medical object in the hollow organ on the basis of the dataset;
- wherein the signal is provided in addition as a function of the identified meandering, spiraling, or meandering and spiraling of the medical object in the hollow organ.

14. The method of claim 11, wherein the sensor of the reference unit is configured to detect a plurality of coefficients of friction along a longitudinal extension direction of the medical object; wherein a movement of the medical object relative to the reference unit by the mover device has taken place prior to commencement of the method; wherein the virtual frictional force is simulated on the basis of the dataset and the plurality of coefficients of friction as a function of a spatial positioning of the distal end portion of the medical object in the examination subject.

15. The method of claim 11, further comprising:
- controlling a renewal unit as a function of the signal for renewing a surface of the medical object in order to reduce a coefficient of friction of the surface.

16. A non-transitory computer implemented storage medium, including machine-readable instructions stored therein, that when executed by at least one processor, cause the processor to:
- receive, after moving, holding, or moving and holding of a medical object by a mover device, wherein the medical object is disposed in a hollow organ of an examination subject, a sensor signal of a sensor unit configured to detect a counterforce exerted by the medical object on the mover device and acting in the opposite direction to a force of the mover device, wherein the sensor signal contains information relating to the counterforce;

receive a reference signal of a reference unit, wherein the reference unit comprises a sensor configured to detect at least one coefficient of friction of the medical object at the mover device and/or at an introducer sheath for introducing the medical object into the examination subject;

simulate a virtual frictional force between the medical object and the hollow organ on the basis of the at least one coefficient of friction;

receive a dataset that contains an image of the examination subject;

determine a spatial positioning of a distal end portion of the medical object with respect to the dataset;

identify an origin of the counterforce on the basis of the sensor signal, the spatial positioning of the distal end portion, the reference signal, the virtual frictional force, and the dataset; and provide the signal as a function of the origin of the counterforce.

17. The non-transitory computer implemented storage medium of claim 16, wherein determining additionally comprises:
    identifying an obstacle in the hollow organ at the distal end portion as the origin of the counterforce on the basis of the dataset; or
    identifying a frictional force between the hollow organ and the medical object as the origin of the counterforce by ruling out the obstacle in the hollow organ on the basis of the dataset.

18. The non-transitory computer implemented storage medium of claim 17, wherein the dataset further contains a model of the examination subject and of the medical object; wherein determining comprises determining the spatial positioning a distal end portion of the medical object in the dataset.

* * * * *